(12) United States Patent
Chaudoreille et al.

(10) Patent No.: US 10,481,060 B2
(45) Date of Patent: Nov. 19, 2019

(54) DENSITY SENSOR AND DENSITY SENSOR MANUFACTURING METHOD

(71) Applicant: AVENISENSE, Le Bourget du Lac (FR)

(72) Inventors: Francois Chaudoreille, Gresy sur Aix (FR); Guillaume Granier, Le Bourget du Lac (FR); Lucia Jimenez, Grenoble (FR)

(73) Assignee: WIKA TECH, Le Bourget-du-Lac (FR)

( * ) Notice: Subject to any disclaimer, the term of this patent is extended or adjusted under 35 U.S.C. 154(b) by 299 days.

(21) Appl. No.: 15/273,014

(22) Filed: Sep. 22, 2016

(65) Prior Publication Data

US 2017/0082527 A1 Mar. 23, 2017

(30) Foreign Application Priority Data

Sep. 22, 2015 (EP) ..................................... 15306476

(51) Int. Cl.
*G01N 9/00* (2006.01)
*G01N 9/10* (2006.01)
*G01N 11/16* (2006.01)
*G01D 11/30* (2006.01)

(52) U.S. Cl.
CPC ............. *G01N 9/002* (2013.01); *G01D 11/30* (2013.01); *G01N 11/16* (2013.01)

(58) Field of Classification Search
CPC ................................ G01N 11/16; G01N 9/002
See application file for complete search history.

(56) References Cited

U.S. PATENT DOCUMENTS 3,718,566 A * 2/1973 Krebs .................. G01N 27/404
  204/415
4,114,423 A * 9/1978 Wenger .................. G01N 9/002
  73/24.05

(Continued)

FOREIGN PATENT DOCUMENTS

EP 1804048 B1 5/2010
EP 1698880 B1 10/2011
WO WO2013153224 A1 10/2013

OTHER PUBLICATIONS

EP15306476 Extended European Search Report, dated Feb. 16, 2016, European Patent Office, 80298 Munich, Germany.

*Primary Examiner* — Herbert K Roberts
(74) *Attorney, Agent, or Firm* — The Jansson Firm; Pehr B. Jansson

(57) ABSTRACT

A density sensor to measure the density of a gas having a density ranging from 30 gram per cubic meter to 150 kilogram per cubic meter and a working pressure ranging from 0 to 100 bar. The density sensor includes a resonator housing, a membrane, an actuating/detecting module mechanically coupled to the membrane, and a resonating element arranged to be immersed in the gas, the resonating element being mechanically coupled to the membrane by a pedestal. The resonating element is a resonating disk having a thickness ranging from 25 μm to 200 μm and a diameter ranging from 4 mm to 12 mm. The resonating disk extends parallelly to the membrane or being angled relatively to the membrane and is coupled by its center to the pedestal. The resonating disk is made of a metal chosen among the group comprising stainless steel, nickel-iron alloy and Molybdenum.

10 Claims, 9 Drawing Sheets

(56) References Cited

U.S. PATENT DOCUMENTS

| | | | | |
|---|---|---|---|---|
| 4,922,745 | A | * | 5/1990 | Rudkin .................. G01N 9/002 73/32 A |
| 5,345,811 | A | * | 9/1994 | Alexandrovich, Sr. ...................... G01N 9/002 73/32 A |
| 7,874,199 | B2 | | 1/2011 | Chaudoreille |
| 7,958,772 | B2 | | 6/2011 | Permuy |
| 2003/0183888 | A1 | * | 10/2003 | Bar-Sadeh ............... H04R 7/02 257/419 |
| 2008/0092637 | A1 | * | 4/2008 | Cho ....................... G01N 11/16 73/54.41 |
| 2008/0156093 | A1 | * | 7/2008 | Permuy .................. G01N 9/002 73/32 A |
| 2008/0257036 | A1 | * | 10/2008 | Chaudoreille ......... G01N 9/002 73/32 A |
| 2009/0120169 | A1 | * | 5/2009 | Chandler, Jr. ......... G01N 9/002 73/54.41 |
| 2010/0060111 | A1 | | 3/2010 | Ayazi |
| 2011/0063041 | A1 | | 3/2011 | Yamada |

* cited by examiner

DENSITY SENSOR AND DENSITY SENSOR MANUFACTURING METHOD

TECHNICAL FIELD

The invention relates to a density sensor and its manufacturing method. The invention is particularly applicable to the measurement of density, specific gravity and molecular weight of gas.

BACKGROUND

The density of a fluid ($\rho$) is defined as its mass per unit volume. Mathematically, density is simply defined as mass (m) divided by volume (V): $\rho=m/V$. The SI (International System) unit for density is kg.m$^{-3}$ (kilogram per cubic meter). It is more commonly expressed in g.cm$^{-3}$ or g/cc (gram per cubic centimeter), a thousandth of the SI. Typical values for most liquids range between 0.6 g.cm$^{-3}$ and 1.3 g.cm$^{-3}$. For gases, the most commonly used unit for density is g.m$^{-3}$ (gram per cubic meter), with typical range between 30 g.m$^{-3}$ (low pressure hydrogen-based applications) and 150 kg.m$^{-3}$ (process applications). There is a ratio ranging from 500 to 1000 between liquid density and gas density. Further, higher gas densities can be found when reaching high pressure or very low temperature, as for Liquefied Natural Gas (LNG).

The specific gravity (SG) is the ratio of the density of a substance to the density of a reference substance. For liquids, SG is the ratio of the density of a given fluid to the density of water. For gases, SG is the ratio of the density of a given gas to the density of air. SG must compare fluids within the same pressure and temperature conditions. It is a dimensionless quantity, widely used in industry for the determination of concentrations in aqueous solutions, mostly for historical reasons (first industrial tests would only allow comparisons, no direct density estimations).

The document EP1698880 describes a density and viscosity sensor for measuring density and viscosity of fluid, the sensor comprising a resonating element arranged to be immersed in the fluid, an actuating/detecting element coupled to the resonating element, and a connector for coupling to the actuating/detecting element. The sensor further comprises a housing defining a chamber isolated from the fluid, the housing comprising an area of reduced thickness defining a membrane separating the chamber from the fluid. The actuating/detecting element is positioned within the chamber so as to be isolated from the fluid and mechanically coupled to the membrane. The resonating element arranged to be immersed in the fluid is mechanically coupled to the membrane. The membrane has a thickness enabling transfer of mechanical vibration between the actuating/detecting element and the resonating element. The resonating element comprises a first beam mechanically coupled to the membrane by a mechanical coupling element so as to be approximately parallel to the area of the sensor housing contacting the fluid to be measured.

The documents EP1804048, U.S. Pat. No. 7,874,199 and WO2013/153224 also describe density and viscosity sensors for measuring density and viscosity of fluid wherein the resonating element has various possible shapes.

As the resonating element vibrates in the fluid, some of the surrounding fluid is displaced. The effective mass of the resonating element is increased by an amount $\delta m$ determined by the volume of fluid entrained by the moving section. This effect is related to fluid density, and a densitometer is provided. The hereinbefore described density and viscosity sensors are well adapted for the measurement of density and viscosity of liquids. However, they are not well adapted for the measurement of the density of gas because the resonating element is not sensitive enough to be usable. The sensitivity of a resonating element is a report of the relative variation of its resonance frequency as surrounding fluid density is varied. Using a simple spring mass system model, the sensitivity is proportional to the square root of the ratio of the added mass to the intrinsic mass of the resonating element. The density of typical gas such as nitrogen at atmospheric pressure and temperature of 25° C. is around 1 kg/m$^3$, one thousand times less than liquid water density. In practice, resonance characteristics of a resonating element having a paddle shape barely change with gas composition at atmospheric conditions.

SUMMARY OF THE DISCLOSURE

It is an object of the invention to propose a density sensor that overcomes one or more of the limitations of the existing sensors. In particular, it is an object to a density sensor that is particularly well adapted for the measurement of gas density with an appropriate sensitivity.

According to one aspect, there is provided a density sensor to measure the density of a gas having a density ranging from 30 gram per cubic meter to 150 kilogram per cubic meter and a working pressure ranging from 0 to 100 bar comprising:
- a resonator housing defining a chamber isolated from the gas, the resonator housing comprising an area of reduced thickness defining a membrane separating the chamber from the gas;
- an actuating/detecting module positioned within the chamber so as to be isolated from the gas and mechanically coupled to the membrane;
- a resonating element arranged to be immersed in the gas, the resonating element being mechanically coupled to the membrane by a pedestal;

wherein the membrane, the pedestal and the resonator housing are made of metal;

wherein the membrane has a thickness enabling transfer of mechanical vibration between the actuating/detecting module and the resonating element through the pedestal;

and wherein the resonating element is a resonating disk having a large diameter to thickness ratio, in particular a thickness ranging from around 25 μm to 200 μm and a diameter ranging from around 4 mm to 12 mm, the resonating disk extending parallely to the membrane or being angled relatively to the membrane, and being coupled by its center to the pedestal, the resonating disk made of a metal chosen among the group comprising stainless steel, nickel-iron alloy and Molybdenum.

The resonating disk may comprise one surface having a thinned or tapered edge forming a shoulder creating a dissymmetry between its two faces such as to generate an anisotropic resonating disk.

The resonating disk may comprise one surface having at least one undulation creating a dissymmetry between its two faces such as to generate an anisotropic resonating disk.

The pedestal may have a section diameter of around 1 mm.

The actuating/detecting module may comprise a piezoelectric ceramic.

The membrane and the pedestal may be made of a metal chosen among the group comprising stainless steel, nickel-iron alloy and Molybdenum.

The density sensor may further comprise:
an electronics housing defining another chamber isolated from the gas and comprising an electronic board connected to the actuating/detecting module and to a connector; and
a supporting and attaching plate to support and couple together the resonator housing and the electronics housing, and comprising attachment means of the density sensor to a wall.

The resonator housing may further comprises a through-hole extending parallel to a longitudinal axis of the resonator housing close to an external circumference of the resonator housing and emerging in a portion of the sensor arranged to be in contact with the gas to be measured close to the membrane, the through-hole receiving a temperature sensor probe in a sealed manner.

The density sensor may further comprise a protective cover protecting the membrane, the pedestal and the resonating element against solid particles and/or moisture contained in the gas and letting flow the gas around the resonating element, said protective cover comprising a thin metal mesh coated with an hydrophobic polymer.

According to a further aspect, there is provided a method to manufacture a density sensor, the density sensor being arranged to measure the density of a gas having a density ranging from 30 gram per cubic meter to 150 kilogram per cubic meter and a working pressure ranging from 0 to 100 bar and comprising a resonator housing defining a chamber isolated from the gas and an area of reduced thickness defining a membrane, an actuating/detecting module positioned within the chamber and mechanically coupled to the membrane, and a resonating element arranged to be immersed in a gas to be measured and being mechanically coupled to the membrane by a pedestal; wherein the density sensor manufacturing method comprises:
manufacturing the membrane, the pedestal and the resonator housing in a metal;
manufacturing the resonating element under the shape of a resonating disk having a large diameter to thickness ratio, in particular a thickness ranging from around 25 µm to 200 µm and a diameter ranging from around 4 mm to 12 mm, the resonating element being made of a metal chosen among the group comprising stainless steel, nickel-iron alloy and Molybdenum;
positioning the resonating disk onto the pedestal at substantially a center point of the resonating disk such that the resonating disk extends parallely to the membrane or being angled relatively to the membrane; and
electrically welding the resonating disk to the pedestal by applying a welding signal between the resonating disk and the pedestal, said welding signal having a defined intensity, voltage and duration depending on the metal making of the resonating disk. The pedestal may have a section diameter of around 1 mm. For the resonating disk and the pedestal made of stainless steel, the welding may be characterized by a welding intensity ranging from 300 A to 1000 A and a welding time ranging from 3 to 20 ms, and a force of application of a welding electrode ranging from 18 to 25 N. For the resonating disk made of nickel-iron alloy and the pedestal made of stainless steel, the welding may be characterized by a welding intensity ranging from 300 A to 1000 A and a welding time ranging from 5 to 15 ms, and a force of application of a welding electrode ranging from 18 to 25 N. For the resonating disk made of Molybdenum and the pedestal made of stainless steel or Molybdenum, the welding may be characterized by a welding intensity ranging from 300 A to 1600 A and a welding time ranging from 3 to 15 ms, and a force of application of a welding electrode ranging from 20 to 30 N.

The density sensor manufacturing method may further comprise performing an annealing step at a temperature around 800° C. after welding for the resonating disk made of stainless steel.

The density sensor manufacturing method may further comprise performing a resonating disk forming step, during the resonating element manufacturing step, comprising forming a thinned or tapered edge as a shoulder and/or at least one undulation on one surface of the resonating disk so as to create a dissymmetry between its two faces by stamping or laser cutting/engraving.

According to still a further aspect, there is provided a use of a density sensor in accordance with the invention to measure the density of a gas within a tubing or a container, the density sensor being tightly coupled to a wall of a tubing or a container, or immersed into a chamber.

With the invention, it is possible to achieve a density sensor particularly well adapted for measuring the density of gas having:
A robustness whatever the measurement conditions, i.e. temperature variations, pressure peaks, humidity, deposits, etc.;
A robustness during transportation with an improved resistance to shock;
A long-term stability due to the manufacturing process (e.g. welding, heat treatment/annealing, etc . . . );
A capacity to be manufactured with a good manufacturing repeatability under controlled conditions; and
All the metrological performance of the market density sensor or even beyond.

Further, the choice of the metal can be tailored on the type of gas to be measured and measurement context. This enables adapting the density sensor to demanding application, for example in corrosive or high temperature conditions.

Furthermore, the industrialization and cost do not require large investments compared for example to density sensor based on the Micro-Electro-Mechanical Systems (MEMS) technology (i.e. the manufacturing of MEMS requires clean rooms).

Other advantages will become apparent from the hereinafter description of the invention.

BRIEF DESCRIPTION OF THE DRAWINGS

The present invention is illustrated by way of examples and not limited to the accompanying drawings, in which like references indicate similar elements.

DETAILED DESCRIPTION

The invention will be understood from the following description, in which reference is made to the accompanying drawings.

Figure 1:
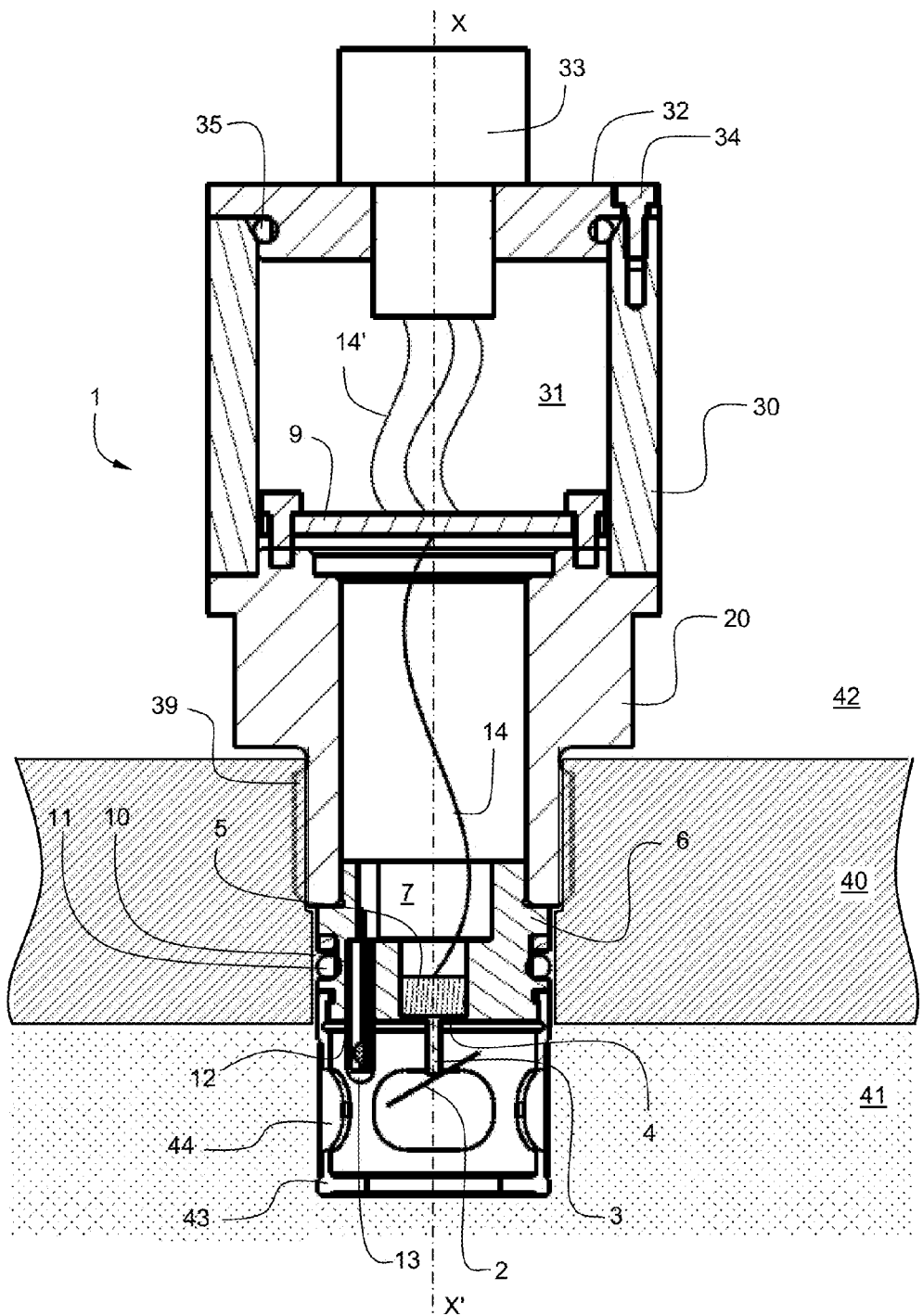
FIGS. 1, 2 and 3 is a cross-section side view, a perspective top view and perspective bottom view schematically illustrating a density sensor according to a first embodiment of the invention, respectively.
Figure 2:
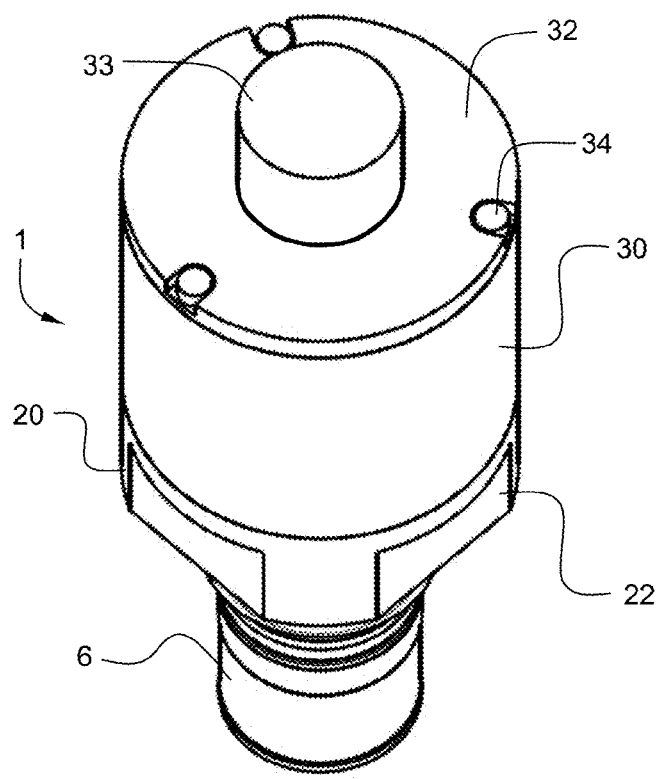
Figure 3:
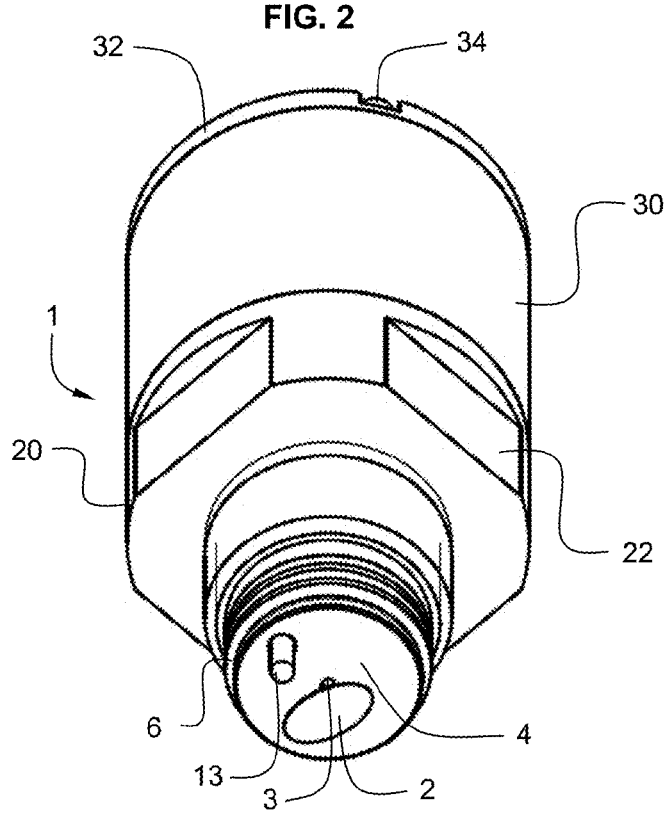
Figure 4:
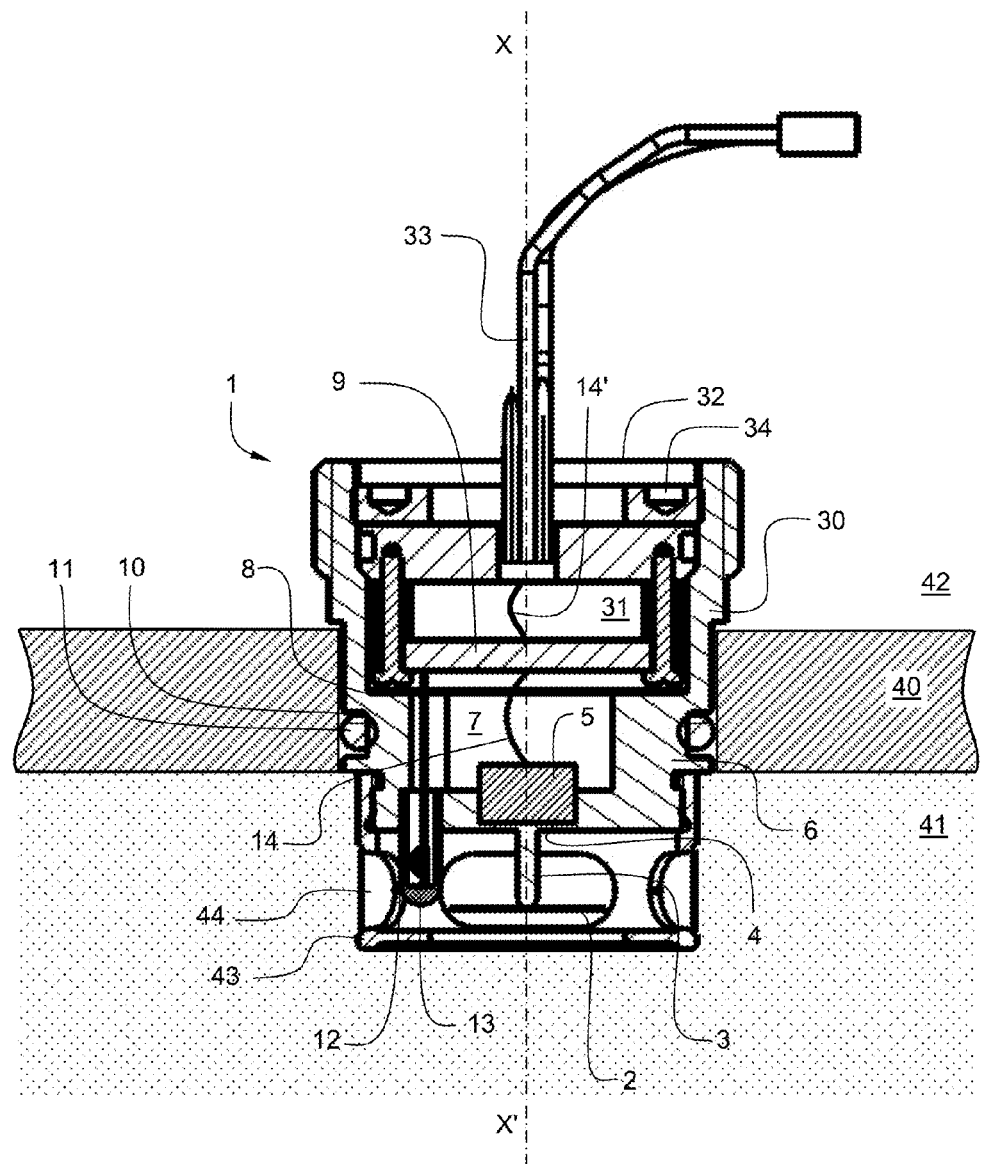
FIGS. 4, 5, 6 and 7 is a cross-section side view, a side view, a perspective top view and perspective bottom view schematically illustrating a density sensor according to a second embodiment of the invention, respectively.
Figure 5:
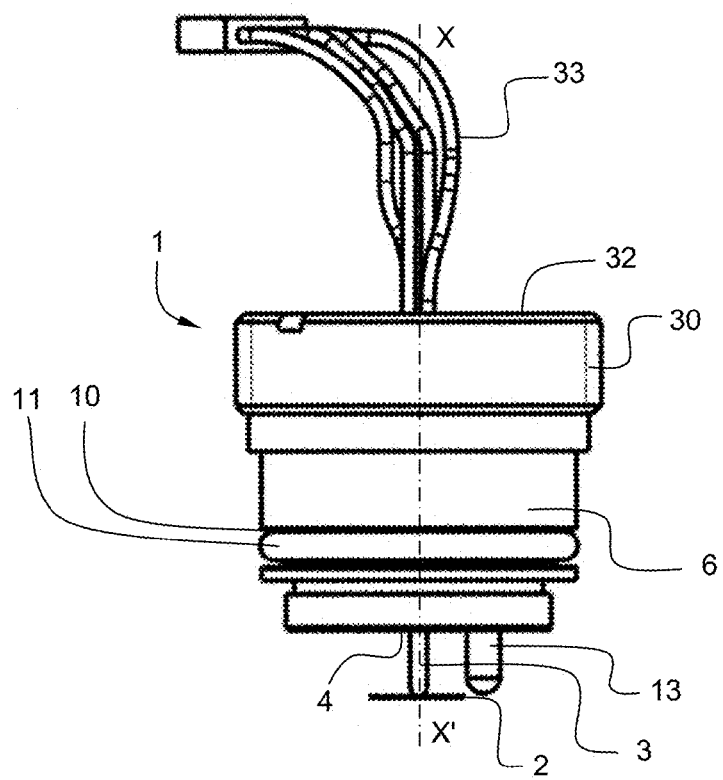
Figure 6:
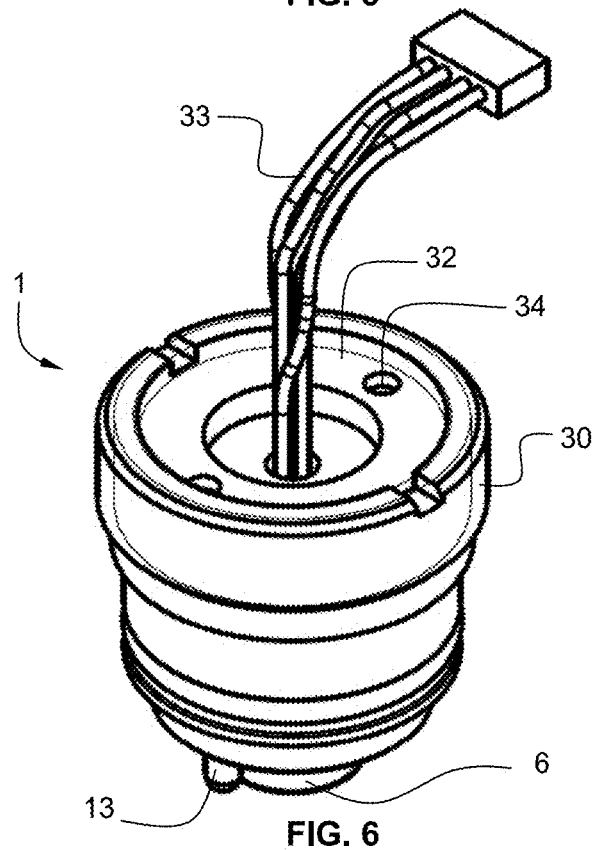
Figure 7:
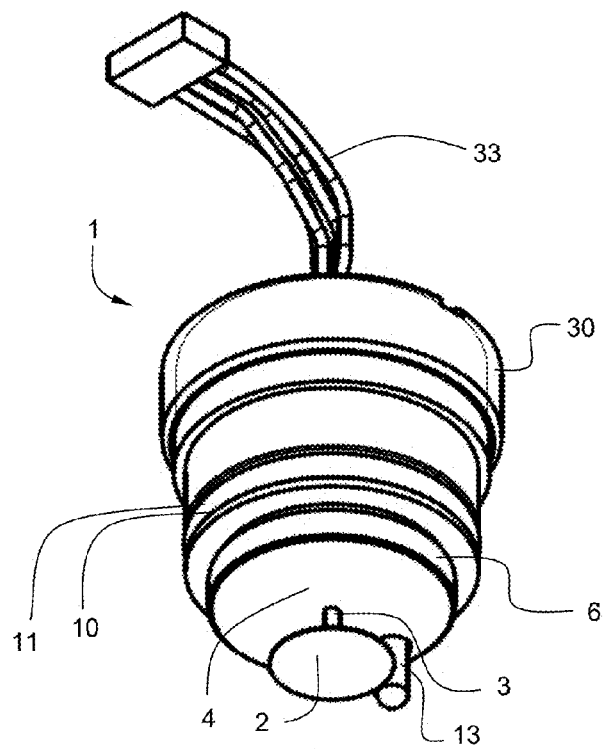

FIGS. 1-3 show a density sensor 1 according to a first embodiment of the invention. FIGS. 1, 2 and 3 depict a cross-section side view, a perspective top view and a perspective bottom view of said embodiment of the density sensor 1, respectively.

The density sensor 1 comprises a resonating element 2, a pedestal 3, a membrane 4, an actuating/detecting module 5, a resonator housing 6 defining a first chamber 7, a supporting and attaching element 20, an electronics housing 30 defining a second chamber 31, a connector 33, an electronic board 9 and a temperature sensor probe 13.

The resonator housing 6 has a substantially cylindrical shape of longitudinal symmetry axis XX'. The resonator housing 6 is made of metal or metallic alloy, for example in stainless steel 316L, Inconel, Hastelloy, Molybdenum, etc . . . The resonator housing 6 comprises a groove 10 extending on an external circumference of the resonator housing 6. The groove 10 receives an O-ring type sealing 11. Other type of sealing may be possible. Therefore, this portion of the resonator housing 6 is arranged to be tightly inserted and secured to a hole of a wall 40 of a pipe, a chamber, or a container, etc . . . . The sealing separates a portion of the sensor arranged to be in contact with the gas to be measured (gas side 41) from a portion of the sensor (connector side 42) arranged to be connected to external equipment (lab & process equipments, analyzers, industrial installations, etc . . . ). The gas side 41 may be submitted to harsh environment (high pressure, high temperature, and/or corrosive gas . . . ). The connector side 42 may be at the atmospheric pressure. Typically, the density of a gas to be measured ranges from 30 gram per cubic meter to 150 kilogram per cubic meter and the working pressure of the density sensor (pressure at the gas side 41) ranges from 0 to 100 bar (absolute).

The resonator housing 6 defines a first chamber 7 under the form of an internal cavity. The first chamber 7 is isolated from the gas side 41 by the membrane 4. The membrane 4 is a part of the resonator housing 6 having a reduced thickness orientated towards the portion of the sensor arranged to be in contact with the gas to be measured (i.e. the gas side 41). The membrane 4 extends perpendicularly to the longitudinal symmetry axis XX'.

The first chamber 7 has a general hollow cylindrical shape. The first chamber 7 receives the actuating/detecting module 5. More precisely, the actuating/detecting module 5 is mounted inside the first chamber 7 onto the membrane 4. In the present embodiment, the actuating/detecting module 5 is a disk shaped piezoelectric element that extends perpendicularly to the longitudinal symmetry axis XX'. The disk shaped piezoelectric element 5 is made of a piezoelectric ceramic, for example a Lead Zirconate Titanate piezoceramic disk. The disk shaped piezoelectric element 5 has a front side (directed towards the membrane 4) and a back side (directed towards the internal cavity formed by the first chamber 7). The front side is mechanically and electrically coupled to the membrane 4. The back side is connected to the electronic board 9 by a wire 14. The front side is connected to an electrical ground by means of the membrane 4 and the resonator housing 6 (both being made of a conductive material). The disk shaped piezoelectric element 5 is mainly working in extension.

The resonating element 2 is coupled to the membrane 4 by a pedestal 3. The resonating element 2 is a resonating disk (i.e. a flat circular/elliptical shape) that is attached substantially at its center to the pedestal 3. Theoretical analysis demonstrates that resolution and sensitivity to gas can be achieved using extremely thin disk shapes. The added mass is related to the cube of the diameter of the resonating disk while the intrinsic resonator mass is proportional to the square of the diameter multiplied by the thickness of the resonating disk. As a consequence a large diameter to thickness ratio is favorable for density measurement, for example the resonator disk has a thickness ranging from around 25 μm to 500 μm and a diameter ranging from around 4 mm to 12 mm. A resonating disk made of metal is well adapted to the density measurements of corrosive gas, and also resistant to mechanical shocks and operational vibrations. Typically, for manufacturing reasons, the resonating disk and the pedestal are separate pieces. Depending on the material making of the resonating disk and the pedestal, the process of assembling the resonating disk and the pedestal may differ. Various techniques may be used like welding, gluing, brazing techniques, etc . . . A particular manufacturing step using electric welding will be explained in details hereinafter. Further, the pedestal 3 may form an integral part with the membrane 4, or may be a separate piece attached to the membrane 4. The pedestal 3 is positioned onto the membrane 4, for example at substantially a center point of the membrane. The pedestal 3 serves to position the resonating disk 2 into the gas to be measured. Therefore, the resonating disk 2 is fully immersed and surrounded by the gas. The pedestal 3 further serves to mechanically couple the membrane 4 to the resonating element 2 so as to transmit vibration from the membrane 4 to the resonating disk 2, and vice-versa. In the first embodiment, the resonating disk 2 is positioned at an angle of 60° relatively to the longitudinal symmetry axis XX' (or 60° relatively to the membrane 4). The pedestal is positioned parallely to the longitudinal symmetry axis XX', and perpendicularly to the membrane 4.

The resonator housing 6 further comprises a through-hole 12 extending parallel to the longitudinal axis XX' close to the external circumference of the resonator housing 6. The through-hole 12 emerges in the portion of the sensor arranged to be in contact with the gas to be measured (gas side 41) close to the membrane 4. The through-hole 12 receives the temperature sensor probe 13 in a sealed manner and a connecting wire to the electronic board 9. A distal end of the temperature sensor probe 13 is positioned close to the resonating element 2 so as to measure the temperature at the position where the density measurements are performed. The temperature measurements may be used to compensate for temperature effects on density measurements. A high-resolution temperature sensor probe 13 may be a standard PT1000 thermistor.

The electronics housing 30 defines a second chamber 31 under the form of an internal cavity. The second chamber 31 may communicate with the first chamber 7 or be separated by an insulation part. The second chamber 31 is isolated from the external environment. The second chamber 31 has a general hollow cylindrical shape, and receives the electronic board 9. The electronic board 9 is appropriately secured to the electronics housing 30. The electronic board 9 mainly extends perpendicularly to the longitudinal symmetry axis XX' and is positioned close to a front side of the electronics housing 30 close to the resonator housing 6. Further, the second chamber 31 is tightly closed at a back side by a cover plate 32 that is sealingly secured to the electronics housing 30 by means of screw 34 and an O-ring type sealing 35. The cover plate 32 can also we welded, glued or screwed and comprises a centrally positioned hole receiving a feedthrough connector 33 (e.g. a standard coaxial connector). The electronic board 9 is connected to the connector 33 (wire 14') and to the disk shaped piezoelectric module 5 by means of various wires 14.

The supporting and attaching element 20 is used to support and couple together the resonator housing 6 and the electronics housing 30, and also to enables attachment of the density sensor 1 to the wall 40 of a tubing, or a pipe, or a container, or a chamber of an external equipment (lab & process equipments, analyzers, industrial installations, etc . . . ). The supporting and attaching element 20 has a general hollow cylindrical shape extending parallely to the longitudinal symmetry axis XX'. It comprises an appropriate hole for the passage of the connecting wire 14 at substantially its center. It further comprises a threaded portion 21 that enables a secure screwing connection into a hole of the wall 40. It may be faceted so as to define multiple flattenings 22 (see FIGS. 2 and 3) in order to ease the screwing of the whole sensor. As an alternative (not shown), the supporting and attaching element may have a square plate shape comprising multiple through-holes, for example four throughholes, one at each corner used to secure the supporting and attaching element to the wall 40 by means of appropriate screws.

The electronics housing 30 or the supporting and attaching element 20 may also include appropriate electronics temperature insulation means (not shown) in order to avoid the transmission of heat resulting from the operation of the electronic board 9 towards the resonator housing 6, the piezoelectric module 5 and the resonating element 2 resulting in measurement or calibration drifts. The electronics housing 30, the attaching element 20 and the resonator housing 6 can also be one piece.

The chambers 7 and 31 may be filled with a material. Advantageously, the material is a vibration absorbing material (e.g. gas, oil, gel, etc . . . ). The vibration absorbing material enables to reduce perturbation due to parasitic vibration modes of the housings, in particular the resonator housing 6. The chambers 7 and 31 are sealed relatively to the external environment via the cover plate 32 and the connector 33.

The portion of the sensor arranged to be in contact with the gas to be measured (gas side 41), namely the membrane 4, the pedestal 3 and the resonating element 2 may be further protected by a protective cover 43. The protective cover 43 may have the shape of a tube closed at the distal end and comprising multiple holes 44 for letting flow the gas around the resonating element 2. The protective cover 43 is only visible in FIG. 1 and has been omitted in FIGS. 2 and 3 for sake of drawings clarity. Alternatively, the protective cover 43 may be formed of a thin metal mesh, thus porous so as to allow the gas to flow through without solid particles and/or fouling. In addition, the mesh can be coated with an hydrophobic polymer (for example Teflon) in order to avoid the penetration towards the sensitive element of moisture condensed form.

FIGS. 4-7 show a density sensor 1 according to a second embodiment of the invention. FIGS. 4, 5, 6 and 7 depict a cross-section side view, a side view, a perspective top view and a perspective bottom view of said embodiment of the density sensor 1, respectively. The density sensor 1 according to the second embodiment differs from the first embodiment in that:

It is compacter, the electronics housing 30 and the supporting and attaching element 20 having been merged together reducing the overall height of the density sensor;

The connector 33 is a four wires connector;

The resonating disk 2 is positioned at an angle of 90° relatively to the longitudinal symmetry axis XX' (i.e. parallel to the membrane 4); and It can be quickly plug into or unplug from a hole of the wall 40, or screwed.

Figure 18:
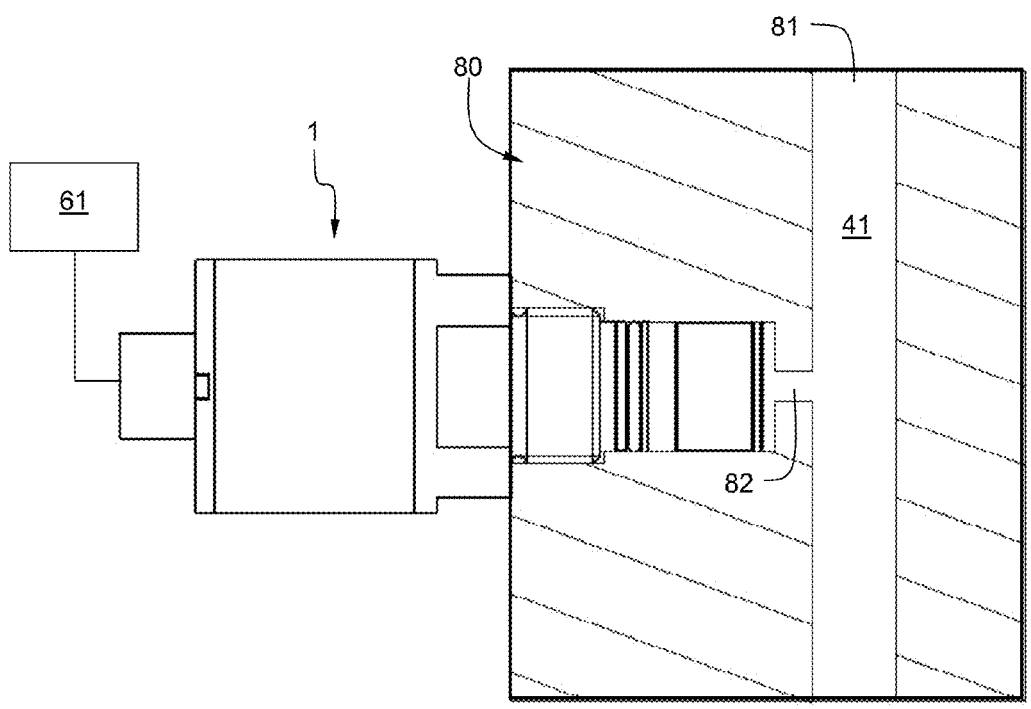

FIGS. 14, 15, 16, 17 and 18 show various application examples where the density sensor is attached to a pipe 60 (FIG. 14), or to a microanalysis pipe 70 (FIGS. 15 and 16), or to a flow line 80 in a flow-through configuration (FIG. 17) or in a flow-by configuration (FIG. 18). The density sensor 1 is connected to a processing device 61 of the external equipment by means of the connector 33. In the flow-through configuration (FIG. 17), the portion of the density sensor comprising the resonating element is projecting inside the tubing 81 so as to position the sensitive element into the flowing gas. In the flow-by configuration (FIG. 18), the flow line comprises a side chamber 82, the portion of the density sensor comprising the resonating element is projecting inside the chamber 82 so as to avoid positioning the sensitive element into the flowing gas. This is particularly advantageous when the flowing gas is a fouling gas or a gas comprising particles because the gas diffuses into the chamber 82 while particles continue travelling into the tubing 81. Thus, fouling gas or a gas comprising particles may result in deposit onto the sensitive element or even clogging inside the tubing 81 in the flow-through configuration (FIG. 17) while such situation is significantly reduced in the flow-by configuration (FIG. 18). The density sensor is not limited to the above mentioned examples where gas are flowing as other application examples are possible, e.g. the density sensor may be fixed by a mechanical holder inside a chamber or a container containing static gas (this application example is not shown in the drawings).

The operation of the density sensor in order to determine the density of gas will be briefly described hereinafter as it is not germane to the present invention and also well known in the art. The first electronic board 9 comprises an appropriate electronics (oscillator module, amplifier module, detection module, processing module, etc . . . ) that performs alternatively an excitation phase and a detection phase.

In a first step, the oscillator applies an excitation signal to the piezoelectric module 5. This results in the application of displacements by the piezoelectric module 5 to the membrane 4, to the pedestal 3 and to the resonating disk 2. The excitation signal is typically a sinusoidal signal in the range of a few Volts to a few hundred Volts. As a consequence, the resonating disk 2 is driven into vibration. Once the excitation is removed, a reception signal representative of the vibration of the resonating disk 3 into the gas can be measured. Conversely to the excitation phase, in the detection phase, the attenuation of the vibration of resonating disk 2 into the gas transmitted to the piezoelectric module 5 via the pedestal 3 and the membrane 4 generates a reception signal that is related to the vibration of the resonating disk 2. The reception signal is typically a sinusoidal signal around a few micro-Volts. The reception signal is amplified and processed. The resonance frequency is determined. The density of gas is determined by comparison with calibration measurements. Also, the calculation integrates the gas temperature in order to compensate for resonator stiffness changes with temperature. The temperature measurement is performed by the temperature sensor probe 13 installed close to the resonating disk (In Situ temperature). As usual in the art, the density sensor is calibrated after manufacturing by measuring multiple resonances for different kind of gas (calibration gas for which densities are well known) and also for various temperatures and pressures (defined temperature and pressure ranges).

A density sensor of the invention is well adapted for measuring the relative density of gas ranging from 30 g.m$^{-3}$ to 150 kg.m$^{-3}$ and molar mass ranging from 2 g.mol$^{-1}$ to 50 g.mol$^{-1}$ with an accuracy for the relative density around 2.5 g.m$^{-3}$+0.08%$_{reading}$ (typical) or around 5 g.m$^{-3}$+0.2%$_{reading}$ (maximum), for the molar mass around 0.8%$_{F.S.}$ (typical) or around 2%$_{F.S.}$ (maximum), and a repeatability for viscosity around 0.01%$_{F.S.}$ and for density around 0.1%$_{F.S.}$ (F.S. stands for Full Scale).

When manufacturing the density sensor, two aspects concern manufacturing the resonating disk 2 (resonating element) and attaching the resonating disk 2 to the membrane 4 though the pedestal 3. The resonating disk 2 and the pedestal 3 are separate pieces. In the present example, the pedestal 3 forms an integral part with the membrane 4. In this case, the pedestal and the membrane 4 are machined together. Both can be made of metallic materials, for example stainless steel 316L, Inconel, Hastelloy, Molybdenum, etc . . . . The pedestal 3 is positioned at substantially a center point of the membrane 4. The resonating disk 2 is a metallic disk manufactured out of machined metal films. The resonating disk 2 is made of metal chosen among the group comprising stainless steel, nickel-iron alloy and Molybdenum.

Figure 10:
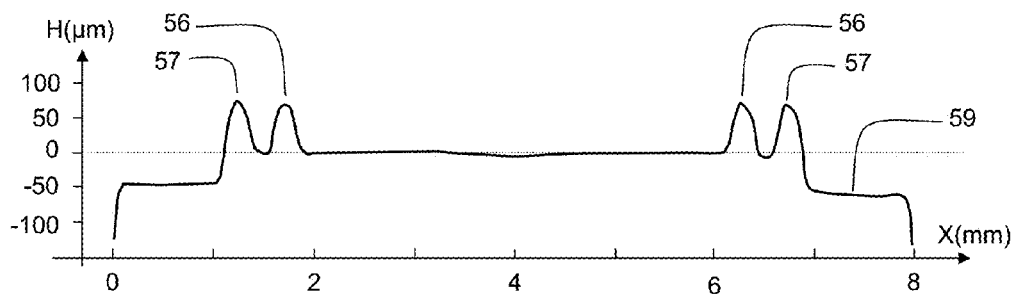
FIGS. 10, 11 and 13 are profile graphics related to FIGS. 9 and 12 illustrating resonating disk profile undulations used to generate an anisotropic resonating disk, said disk being stamped (FIG. 10), or laser cut (FIGS. 11 and 13) and made of stainless steel, nickel-iron alloy and Molybdenum, respectively.
Figure 11:
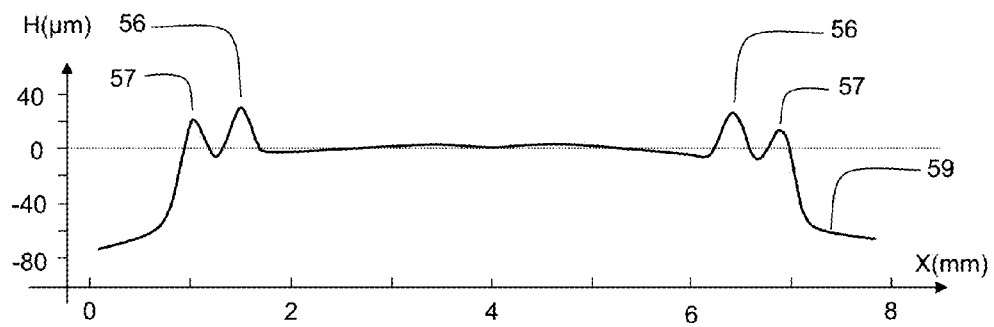
Figure 13:
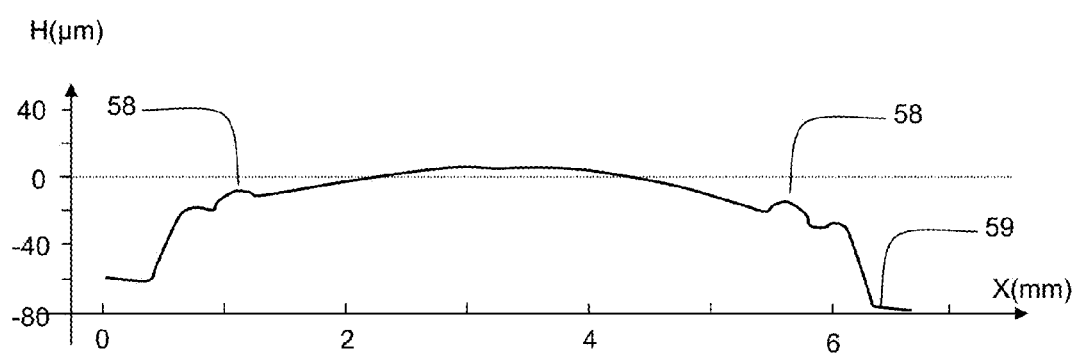
Figure 14:
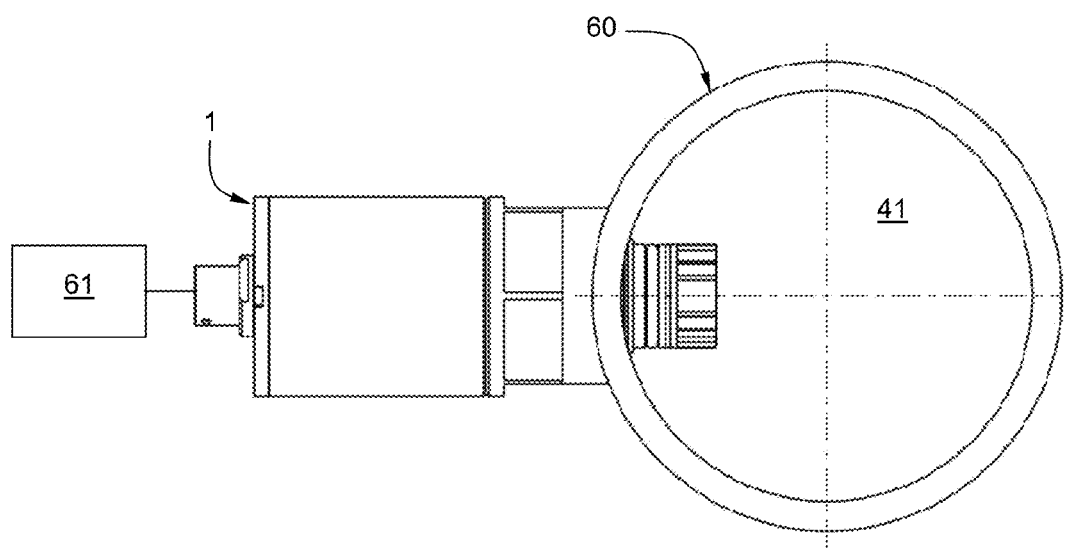
FIGS. 14, 15, 16, 17 and 18 schematically illustrate various sensor installations.
Figures 15, 16:
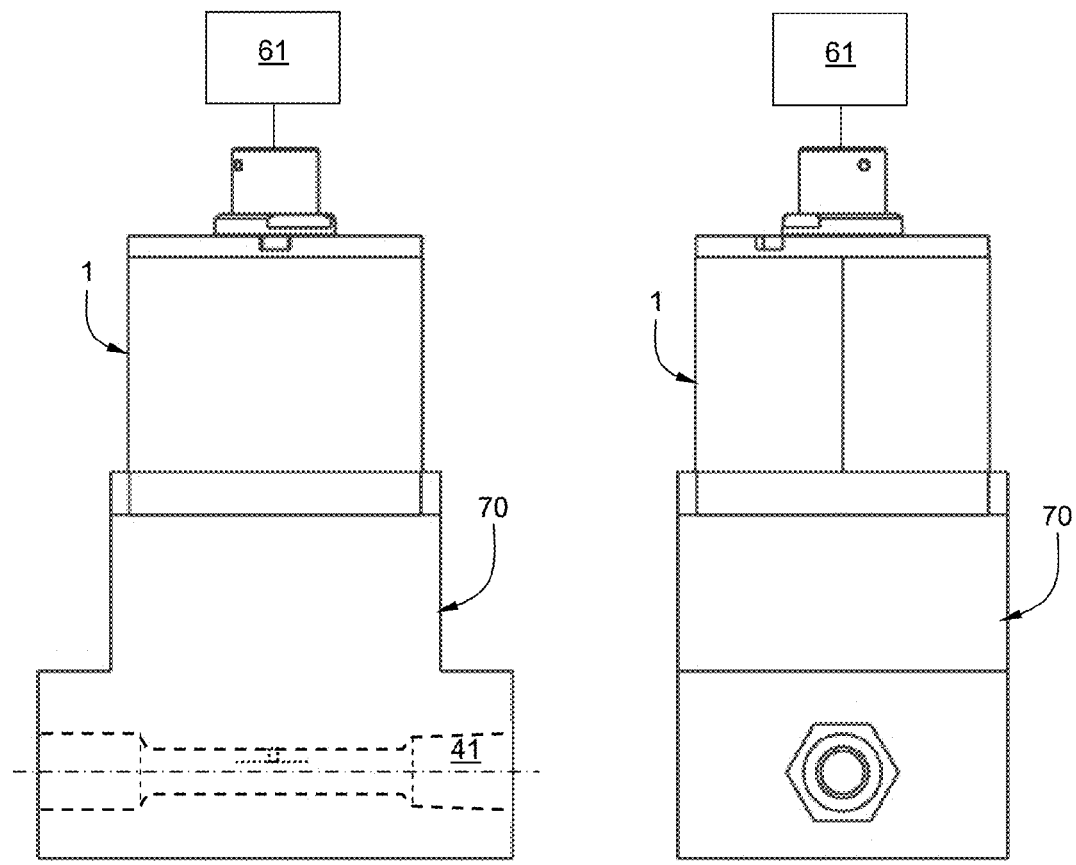
Figure 17:
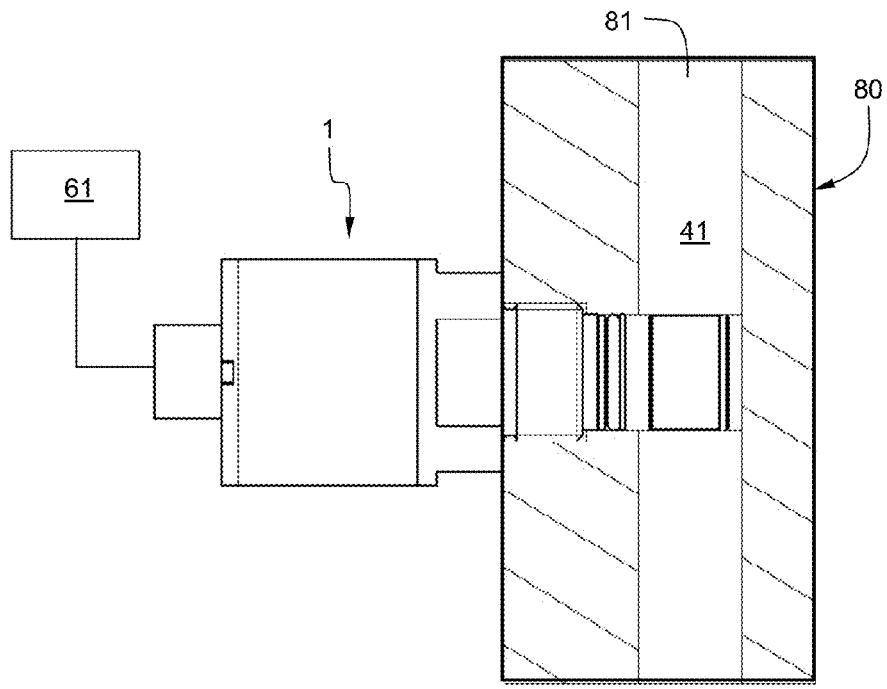

The resonating disk 2 is a disk having a large diameter to thickness ratio, one surface being modified such as to create profile undulations 56, 57, 58 illustrated in FIGS. 10, 11 and 13. The undulations may comprise one (58), two (56, 57) or more (not shown) waves. The undulations profile is not related to the metal making of the resonating disk. The profile undulations create an anisotropic resonating disk, namely a resonating disk having a dissymmetry between its two faces (top/bottom faces). It has been observed that this dissymmetry generates a particular resonance of the resonating disk. Such profile undulations can be realized by stamping the disk (as depicted in FIGS. 10, 11 and 13) or alternatively by laser engraving the disk (not shown). Undulations 56, 57 visible in FIG. 10 have a height H around 50 μm above the height at the center of the resonating disk 2, and a difference of height H around 60 μm between the center and the periphery of the resonator disk 2. The shoulders at both ends are resulting from the stamping process. Undulations 56, 57 visible in FIG. 11 have a height H around 32 μm above the height at the center of the resonating disk 2, and a difference of height H around 63 μm between the center and the periphery of the resonator disk 2. The laser cutting process does not generated shoulders at both ends, the edge 59 of the disk being thinned or tapered. The undulation 58 visible in FIG. 13 has a height H ranging around 4-9 μm, and a difference of height around 20 μm between the center and the periphery of the resonator disk 2. Alternatively, laser engraving techniques and mechanical cutting by stamping can be used to generate the thinned or tapered edge 59 that also creates a dissymmetry in the resonating disk without requiring the undulations 56, 57, 58.

Then, according to a preferred manufacturing step, an electric welding process takes place. It gives satisfactory results in term of attachment and in term of repeatability when manufacturing batches of density sensors. Depending on the material making of the resonating disk, the process of assembling the resonating disk and the pedestal by electric welding differs with respect to the welding intensity, electrode application force and duration.

Figure 8:
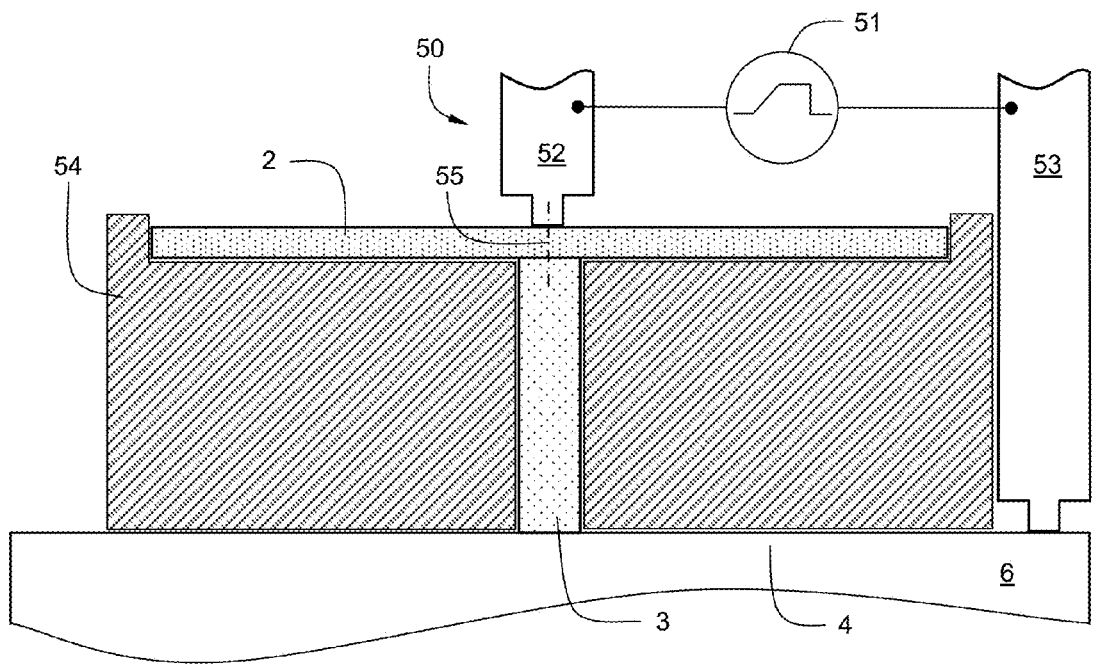
FIG. 8 is a partial side view schematically illustrating a way of coupling the resonating element of the density sensor of FIG. 4 by electric welding.

FIG. 8 is a partial side view schematically illustrating a way of attaching the resonating disk 2 to the membrane 4 though the pedestal 3 in order to manufacture the density sensor by electric welding. The resonating disk 2 is attached substantially at its center (axis 55) to the pedestal 3. It is firstly properly positioned by means of a positioning and holding tool 54. The positioning and holding tool 54 comprises two half parts (cylindrical or parallelepiped) with a central hole so as to be removably positioned around the pedestal 3, and a top countersink (cylindrical lodgment) so as to receive the resonating disk 2. The welder machine 50, for example a welder MYIACHI 5 Khz, 5000 A comprises two electrodes 52, 53 having a plain cylindrical shape ending by a contacting end. Both electrodes 52, 53 are connected to a generator 51 providing a welding signal having defined intensity, voltage and duration. The first electrode 52 is forced to contact the resonating disk 2 at its center (axis 55) at the side opposite to the pedestal 3. The second electrode 53 is forced to contact the housing 6, for example at a periphery of the membrane where place is available. Every pieces being in metal, this forms a closed circuit through which the welding signal is applied in a controlled manner. This results in the resonating disk 2 being electrically welded onto the pedestal 3. In this example, the pedestal has a section diameter of around 1 mm. The resonator disk has a thickness ranging from around 25 μm to 500 μm and a diameter ranging from around 4 mm to 12 mm, as particular examples a thickness ranging from 25 μm to 200 μm and a diameter of around 8 mm. Further, it may be advantageous to control the absence of burr machining at the end of the pedestal. Furthermore, it may also be advantageous to control that the end surface of the pedestal is substantially parallel to the surface of the resonating disk (e.g. properly angled in the first embodiment case and good perpendicularity in the second embodiment case) before positioning the resonating disk and performing the welding operation. The advantages of the electrical welding within the above mentioned conditions are the regularity of the welding, a good repeatability when manufacturing a batch of density sensors, and only a minor deformation of the resonator disk after welding.

Figure 9:
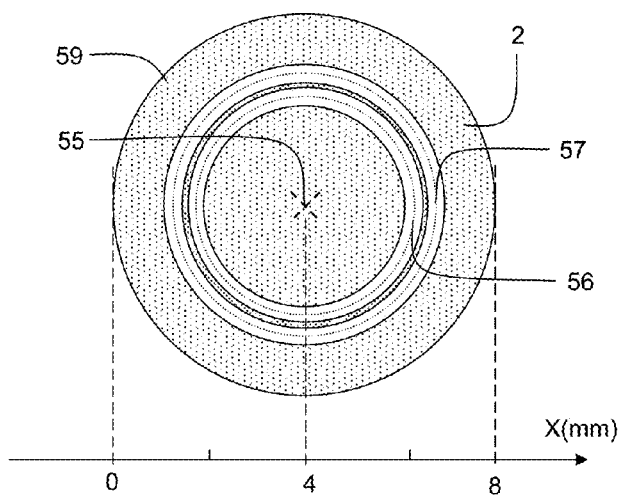
FIGS. 9 and 12 are top views, each schematically illustrating a resonating disk coupled to a pedestal by electric welding.

FIG. 9 is a top view above the resonating disk 2 after the welding step occurs. It shows a resonating disk 2 made of stainless steel or nickel-iron alloy coupled to the pedestal at its center (axis 55) and undulations 56, 57 resulting from the dissymmetry forming process (stamping or laser engraving) performed prior to the welding step.

Figure 12:
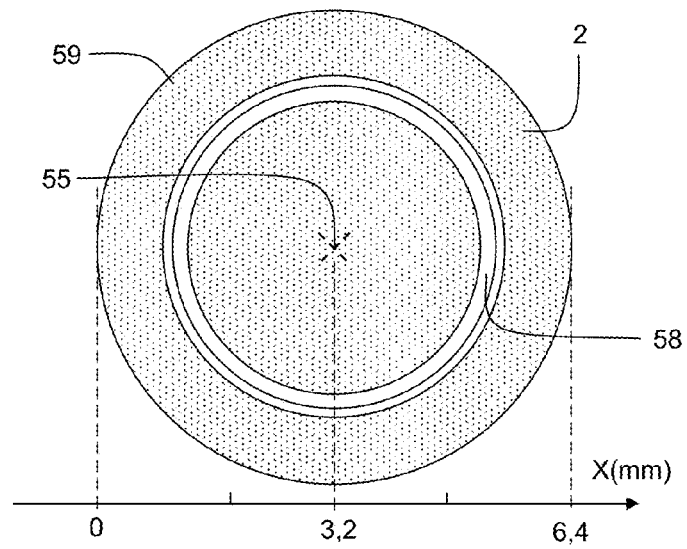

Similarly, FIG. 12 is a top view above the resonating disk 2 after the welding step occurs. It shows a resonating disk 2 made of Molybdenum coupled to the pedestal at its center (axis 55) and undulations 58 resulting from the dissymmetry forming process (laser engraving) performed prior to the welding step.

As a first example, for a resonator disk made of stainless steel (thickness ranging from 25 to 200 μm), the welding characteristic values are a welding intensity ranging between 300 A and 1000 A, a welding voltage around 4 V, a welding time ranging from 3 to 20 ms (this may include around 4 ms of ramp) and a force of application of the welding electrode ranging from 18 to 25 N. When the resonator disk made of stainless steel 316L is welded, a dilatation occurs that affects the long term stability of the density measurements. It has been found that an annealing step after welding at around 800° C. generates a relaxation of the resonator disk that enables recovering the long term stability of the density sensor.

As a second example, for a resonator disk made of nickel-iron alloy (thickness ranging from 25 to 200 µm), the welding characteristic values are a welding intensity ranging between 300 A and 1000 A, a welding voltage around 3 V, a welding time ranging from 5 to 15 ms (this may include around 2 ms of ramp) and a force of application of the welding electrode ranging from 18 to 25 N. Compared to stainless steel 316L, the manufacturing of density sensor comprising a resonating disk made of nickel-iron alloy does not require an annealing step.

As a third example, for a resonator disk made of Molybdenum (thickness ranging from 25 to 200 µm) welded onto a pedestal in stainless steel, the welding characteristic values are a welding intensity ranging between 300 A and 1000 A, a welding voltage around 8 V, a welding time ranging from 3 to 15 ms (this may include around 2 ms of ramp) and a force of application of the welding electrode ranging from 20 to 30 N. For a resonator disk made of Molybdenum (thickness ranging from 25 to 200 µm) welded onto a pedestal in Molybdenum, the welding characteristic values are a welding intensity ranging between 800 A and 1600 A, a welding voltage around 8 V, a welding time ranging from 3 to 10 ms (this may include around 2 ms of ramp) and a force of application of the welding electrode ranging from 20 to 30 N. It may be advantageous to perform two identical and subsequent cycles of welding for welding the resonating disk made of Molybdenum. The welding characteristic values may be adapted when the pedestal, the membrane and the housing are also made of Molybdenum. Compared to stainless steel 316L, the manufacturing of density sensor comprising a resonating disk made of Molybdenum does not require an annealing step. Molybdenum has a temperature of fusion around 1300° C., thus requiring more welding power and welding time. However, the resonating disk made of Molybdenum has a wider range of operation than one made of stainless steel 316L. For example, it is well adapted to the measurement of density of hot gas (100° C.-150° C.) resulting from combustion process (e.g. flare gas used in industrial plants such as hydrocarbon wells or rigs, petroleum refineries, chemical plants and gas processing plants).

The drawings and their description hereinbefore illustrate rather than limit the invention. It should be appreciated that embodiments of the present invention are not limited to embodiments showing a resonating disk 2 extending parallelly to the membrane 4 or inclined with an angle of 30° relatively to the membrane surface, other angles being possible without departing from the scope of the present invention. The invention is not limited to disk shaped piezoelectric element 5 as other type of piezoelectric element may be appropriate, like ring shaped piezoelectric element, superposed or stack of multiple piezoelectric elements, etc . . .

The invention finds application in various industry domains, for example chemical industry, food industry, oil refinery, distribution/transportation of gas/oil, surveillance of industrial rare gases such as required in the pharmaceutical and semiconductor industry, biogas, binary gas mix, etc . . .

The invention claimed is:

1. A density sensor to measure density of a gas having a density ranging from 30 gram per cubic meter to 150 kilogram per cubic meter and a working pressure ranging from 0 to 100 bar comprising:
   a resonator housing defining a chamber isolated from the gas, the resonator housing comprising an area of reduced thickness defining a membrane separating the chamber from the gas;
   an actuating/detecting module positioned within the chamber so as to be isolated from the gas and mechanically coupled to the membrane;
   a resonating element arranged to be immersed in the gas, the resonating element being mechanically coupled to the membrane by a pedestal;
   wherein the membrane, the pedestal and the resonator housing are made of metal;
   wherein the membrane has a thickness enabling transfer of mechanical vibration between the actuating/detecting module and the resonating element through the pedestal;
   wherein the resonating element is a resonating disk having a thickness ranging from 25 µm to 200 µm and a diameter ranging from 4 mm to 12 mm, the resonating disk extending parallelly to the membrane or being angled relatively to the membrane, and being coupled by its center to the pedestal, the resonating disk being made of a metal chosen among a group comprising stainless steel, nickel-iron alloy and Molybdenum; and wherein the resonating disk comprises two opposing major surfaces, one major surface having a thinned or tapered edge forming a shoulder creating a dissymmetry between the two major surfaces such as to generate an anisotropic resonating disk.

2. The density sensor of claim 1, wherein the pedestal has a section diameter of 1 mm.

3. The density sensor of claim 1, wherein the actuating/detecting module comprises a piezoelectric ceramic.

4. The density sensor of claim 1, wherein the membrane and the pedestal are made of a metal chosen among the group comprising stainless steel, nickel-iron alloy and Molybdenum.

5. The density sensor of claim 1, further comprising:
   an electronics housing defining a second chamber isolated from the gas and comprising an electronic board connected to the actuating/detecting module and to a connector;
   a supporting and attaching plate to support and couple together the resonator housing and the electronics housing; and
   means for attaching the density sensor to a wall.

6. The density sensor of claim 1, wherein the resonator housing further comprises a through-hole extending parallel to a longitudinal axis of the resonator housing close to an external circumference of the resonator housing and emerging in a portion of the density sensor arranged to be in contact with the gas to be measured close to the membrane, the through-hole receiving a temperature sensor probe in a sealed manner.

7. The density sensor of claim 1, further comprising a protective cover protecting the membrane, the pedestal and the resonating element against solid particles and/or moisture contained in the gas and letting the gas flow around the resonating element, said protective cover comprising a thin metal mesh coated with a hydrophobic polymer.

8. A density sensor to measure density of a gas having a density ranging from 30 gram per cubic meter to 150 kilogram per cubic meter and a working pressure ranging from 0 to 100 bar comprising:

a resonator housing defining a chamber isolated from the gas, the resonator housing comprising an area of reduced thickness defining a membrane separating the chamber from the gas;

an actuating/detecting module positioned within the chamber so as to be isolated from the gas and mechanically coupled to the membrane;

a resonating element arranged to be immersed in the gas, the resonating element being mechanically coupled to the membrane by a pedestal;

wherein the membrane, the pedestal and the resonator housing are made of metal;

wherein the membrane has a thickness enabling transfer of mechanical vibration between the actuating/detecting module and the resonating element through the pedestal; wherein the resonating element is a resonating disk having a thickness ranging from 25 µm to 200 µm and a diameter ranging from 4 mm to 12 mm, the resonating disk extending parallelly to the membrane or being angled relatively to the membrane, and being coupled by its center to the pedestal, the resonating disk being made of a metal chosen among a group comprising stainless steel, nickel-iron alloy and Molybdenum; and wherein the resonating disk comprises two opposing major surfaces, one major surface having at least one undulation creating a dissymmetry between the two major surfaces such as to generate an anisotropic resonating disk.

9. A method of using a density sensor to measure density of a gas having a density ranging from 30 gram per cubic meter to 150 kilogram per cubic meter and a working pressure ranging from 0 to 100 bar within a tubing or a container comprising:

tightly coupling the density sensor to a wall of the tubing or the container, or immersing the density sensor into a first chamber, said density sensor comprising:

a resonator housing defining a second chamber isolated from the gas, the resonator housing comprising an area of reduced thickness defining a membrane separating the second chamber from the gas;

an actuating/detecting module positioned within the second chamber so as to be isolated from the gas and mechanically coupled to the membrane;

a resonating element arranged to be immersed in the gas, the resonating element being mechanically coupled to the membrane by a pedestal;

wherein the membrane, the pedestal and the resonator housing are made of metal;

wherein the membrane has a thickness enabling transfer of mechanical vibration between the actuating/detecting module and the resonating element through the pedestal;

wherein the resonating element is a resonating disk having a thickness ranging from 25 µm to 200 µm and a diameter ranging from 4 mm to 12 mm, the resonating disk extending parallelly to the membrane or being angled relatively to the membrane, and being coupled by its center to the pedestal, the resonating disk being made of a metal chosen among a group comprising stainless steel, nickel-iron alloy and Molybdenum; and wherein the resonating disk comprises two opposing major surfaces, one major surface having a thinned or tapered edge forming a shoulder creating a dissymmetry between the two major surfaces such as to generate an anisotropic resonating disk;

the method further comprising:
immersing the resonating element into the gas;
transferring mechanical vibration from the actuating/detecting module through the membrane to the resonator via the pedestal;
measuring by the actuating/detecting module a signal representative of the vibration of the resonating element; and
amplifying and processing the signal representative of the vibration of the resonating element by:
determining a resonance frequency; and
determining the density of the gas by comparing the resonance frequency to calibration measurements.

10. A method of using a density sensor to measure density of a gas having a density ranging from 30 gram per cubic meter to 150 kilogram per cubic meter and a working pressure ranging from 0 to 100 bar within a tubing or a container comprising:

tightly coupling the density sensor to a wall of the tubing or the container, or immersing the density sensor into a first chamber, said density sensor comprising:

a resonator housing defining a second chamber isolated from the gas, the resonator housing comprising an area of reduced thickness defining a membrane separating the second chamber from the gas;

an actuating/detecting module positioned within the second chamber so as to be isolated from the gas and mechanically coupled to the membrane;

a resonating element arranged to be immersed in the gas, the resonating element being mechanically coupled to the membrane by a pedestal;

wherein the membrane, the pedestal and the resonator housing are made of metal;

wherein the membrane has a thickness enabling transfer of mechanical vibration between the actuating/detecting module and the resonating element through the pedestal;

wherein the resonating element is a resonating disk having a thickness ranging from 25 µm to 200 µm and a diameter ranging from 4 mm to 12 mm, the resonating disk extending parallelly to the membrane or being angled relatively to the membrane, and being coupled by its center to the pedestal, the resonating disk being made of a metal chosen among a group comprising stainless steel, nickel-iron alloy and Molybdenum; and wherein the resonating disk comprises two opposing major surfaces, one major surface having at least one undulation creating a dissymmetry between the two major surfaces such as to generate an anisotropic resonating disk;

the method further comprising:
immersing the resonating element into the gas;
transferring mechanical vibration from the actuating/detecting module through the membrane to the resonator via the pedestal;
measuring by the actuating/detecting module a signal representative of the vibration of the resonating element; and
amplifying and processing the signal representative of the vibration of the resonating element by:
determining a resonance frequency; and
determining the density of the gas by comparing the resonance frequency to calibration measurements.

* * * * *